United States Patent
Yin et al.

(10) Patent No.: US 9,890,221 B2
(45) Date of Patent: Feb. 13, 2018

(54) CELLULOSE ETHERS ESTERIFIED WITH DICARBOXYLIC ACID

(71) Applicants: Dow Global Technologies LLC, Midland, MI (US); The Regents of the University of Minnesota, Minneapolis, MN (US)

(72) Inventors: Ligeng Yin, Minneapolis, MN (US); Marc A. Hillmyer, Minneapolis, MN (US); Steven J. Guillaudeu, Midland, MI (US); Robert L. Schmitt, Annandale, NJ (US)

(73) Assignees: Dow Global Technologies LLC, Midland, MI (US); University of Minnesota, Minneapolis, MN (US)

( * ) Notice: Subject to any disclaimer, the term of this patent is extended or adjusted under 35 U.S.C. 154(b) by 0 days.

(21) Appl. No.: 14/777,838

(22) PCT Filed: May 7, 2014

(86) PCT No.: PCT/US2014/037070
§ 371 (c)(1),
(2) Date: Sep. 17, 2015

(87) PCT Pub. No.: WO2014/186185
PCT Pub. Date: Nov. 20, 2014

(65) Prior Publication Data
US 2016/0289344 A1    Oct. 6, 2016

Related U.S. Application Data

(60) Provisional application No. 61/822,977, filed on May 14, 2013.

(51) Int. Cl.
| | | |
|---|---|---|
| *C08B 13/00* | (2006.01) | |
| *A61K 9/14* | (2006.01) | |
| *A61K 31/095* | (2006.01) | |
| *A61K 31/4166* | (2006.01) | |
| *A61K 47/38* | (2006.01) | |

(52) U.S. Cl.
CPC .............. *C08B 13/00* (2013.01); *A61K 9/146* (2013.01); *A61K 31/095* (2013.01); *A61K 31/4166* (2013.01); *A61K 47/38* (2013.01)

(58) Field of Classification Search
None
See application file for complete search history.

(56) References Cited

U.S. PATENT DOCUMENTS

| | | |
|---|---|---|
| 4,226,981 A | 10/1980 | Onda et al. |
| 4,316,982 A | 2/1982 | Holst et al. |
| 4,365,060 A | 12/1982 | Onda et al. |
| 4,906,744 A | 3/1990 | Peuscher et al. |
| 5,717,087 A | 2/1998 | Kalbe et al. |
| 2004/0242862 A1 | 12/2004 | Hammes |

FOREIGN PATENT DOCUMENTS

| | | |
|---|---|---|
| EP | 0018605 A2 | 11/1980 |
| EP | 0210917 B1 | 2/1987 |
| EP | 0219426 A2 | 4/1987 |
| EP | 0872233 A1 | 10/1998 |
| EP | 1141029 B1 | 10/2001 |
| WO | 2005115330 A2 | 12/2005 |
| WO | 2009061815 A1 | 5/2009 |
| WO | 2009061821 A2 | 5/2009 |
| WO | 2011159626 A1 | 12/2011 |
| WO | WO 2011/159626 | * 12/2011 |
| WO | WO 2013154607 | * 10/2013 |

OTHER PUBLICATIONS

Breitenbach, Melt extrusion: from process to drug delivery technology, European Journal of Pharmaceutics and Biopharmaceutics, 54, (2002), 107-117.
Kaydos, et al., Preparation of Dimethyl 2-(Phenylthio)maleate, Dimethyl 2-(Phenylthio)fumarate, and Their Sulfoxides, J. Org. Chem., 48, (1983), 1096-1099.
Rowley, et al, Catalytic Double Carbonylation of Epoxides to Succinic Anhydrides: Catalyst Discovery, Reation Scope, and Mechanism, J. Am. Chem. Soc., 129, (2007), 4948-4960.
Bergmeier, et al., Synthesis of Monosubstituted Succinic Acids from tert-Butylsuccinate, Synthesis 10, (2000), 1369-1371.
Yin, et al., Preparation and Performance of Hydroxypropyl Methylcellulose Esters of Substituted Succinates for in Vitro Supersaturation of a Crystalline Hydrophobic Drug, Molecular Pharmaceutics, 11, (2014), 175-185.

* cited by examiner

*Primary Examiner* — Tigabu Kassa

(57) ABSTRACT

Esterified cellulose ethers comprising groups of formula —C(O)—CHR'—CHR"—COOA, wherein, R' and R" are hydrogen or (—S)m(—$R^1$)n-$R^2$, wherein $R^1$ is a hydrocarbon group having 1 to 4 carbon atoms, $R^2$ is an optionally substituted 5- or 6-membered cyclic group, m and n each independently are 0 or 1, and A is hydrogen or a cation, with the proviso that in each group CHR'—CHR" one of R' and R" is hydrogen and the other one is (—S)m(—$R^1$)n-$R^2$, are useful as excipients for maintaining the concentration of poorly water-soluble drugs in aqueous liquids at supersaturation levels.

6 Claims, 5 Drawing Sheets

Scale bars: (a) 5.0 µm and (b) 1.0 µm

Scale bars: 800 nm

Scale bars: 1.0 μm

Scale bars: 800 nm

Scale bars: 600 nm

Scale bars: (a) 10.0 μm and (b) 1.5 μm

Scale bars: 1.5 μm

CELLULOSE ETHERS ESTERIFIED WITH DICARBOXYLIC ACID

FIELD

This invention concerns novel esterified cellulose ethers, solid dispersions of active ingredients in such esterified cellulose ethers, as well as liquid compositions, coated dosage forms and capsules comprising such esterified cellulose ethers.

INTRODUCTION

Esters of cellulose ethers, their uses and processes for preparing them, are generally known in the art. Various known esterified cellulose ethers are useful as enteric polymers for pharmaceutical dosage forms, such as hydroxypropyl methylcellulose acetate succinate (HPMCAS). Enteric polymers are those that are resistant to dissolution in the acidic environment of the stomach. Dosage forms coated with such polymers protect the drug from inactivation or degradation in the acidic environment or prevent irritation of the stomach by the drug.

U.S. Pat. No. 4,365,060 discloses enterosoluble capsules that are said to have excellent enterosolubility behavior. The enterosoluble capsules are shaped with an ester of a cellulose ether that is esterified with acidic succinyl groups and aliphatic monovalent acyl groups, such as HPMCAS.

A large number of presently known drugs have a low solubility in water, and thus complex techniques are required to prepare a dosage form. One known method includes dissolving such drug together with a pharmaceutically acceptable water-soluble polymer in an organic solvent that is optionally blended with water, and to spray-dry the solution. Another method is known as melt extrusion, wherein a drug is blended with a pharmaceutically acceptable water-soluble polymer as a powder blend, the powder blend is heated and intensely mixed in the softened or partially or completely melted state and moved towards a die that shapes the melt as strands, films, pellets, tablets or capsules. The pharmaceutically acceptable water-soluble polymer is aimed at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion.

International Patent Application WO 2005/115330 discloses hydroxypropyl methyl cellulose acetate (HPMCA) polymers and hydroxypropyl methyl cellulose acetate succinate (HPMCAS) polymers with a specific combination of substitution levels. The HPMCAS polymer has a degree of substitution of succinoyl groups ($DOS_S$) of at least 0.02, a degree of substitution of acetyl groups ($DOS_{Ac}$) of at least 0.65 and a sum of $DOS_{Ac}$ and $DOS_S$ of at least 0.85. The HPMCA polymer has a degree of substitution of acetyl groups ($DOS_{Ac}$) of at least 0.15. WO 2005/115330 discloses that the increased acetate substitution allows increased solubility of active agents in spray-dried solutions, while the increased succinate substitution increases the solubility of the polymer in aqueous solution.

International Patent Application WO 2011/159626 discloses an active ingredient and HPMCAS having a degree of substitution of methoxy groups ($DS_M$) of $\leq 1.45$, and a combined degree of substitution of acetyl groups ($DS_{Ac}$) and succinoyl groups ($DS_S$) of ($DS_{Ac}+DS_S$)$\geq 1.25$.

While HPMCAS has shown to be effective at improving the solubility of several drugs in aqueous liquids, the structure of HPMCAS is very complex. To produce HPMCAS, two etherifying agents and two esterifying agents are caused to react with the cellulose backbone, which is a structure of β-1,4 glycosidically bound D-glucopyranose repeating units, designated as anhydroglucose units. The anhydroglucose units have three hydroxy groups that can react with the two etherifying agents and two esterifying agents, which leads to many variables in the HPMCAS structure. Therefore, the precise control of the HPMCAS composition and clear definition of the molecular structure require much effort to understand and optimize this system.

It is an object of the present invention to find other agents which are effective at improving the solubility of drugs in aqueous liquids but which are less complex than HPMCAS.

SUMMARY

Figure 1:
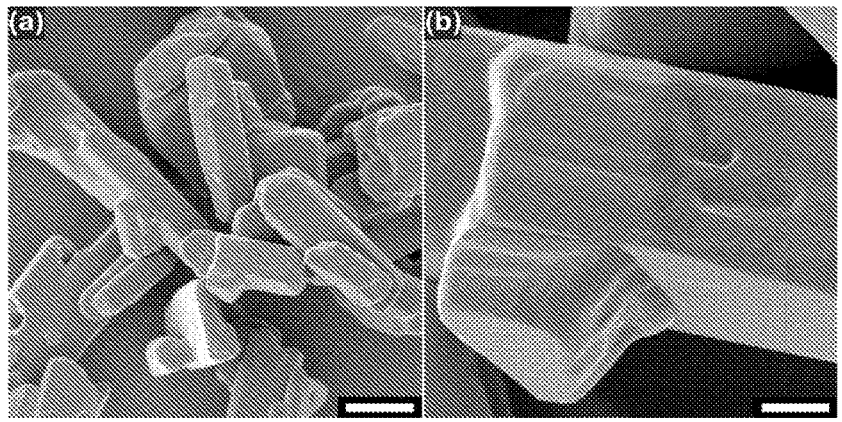
FIG. 1 represents scanning electron microscopy (SEM) pictures of the crystalline drug phenytoin.

Surprisingly, novel esterified cellulose ethers have been found which are effective at improving the solubility of drugs in aqueous liquids but which are less complex than HPMCAS.

Accordingly, one aspect of the present invention are esterified cellulose ethers comprising groups of formula —C(O)—CHR'—CHR"—COOA, wherein R' and R" are hydrogen or $(-S)_m (-R^1)_n-R^2$, wherein $R^1$ is a hydrocarbon group having 1 to 4 carbon atoms, $R^2$ is an optionally substituted 5- or 6-membered cyclic group, m and n each independently are 0 or 1, and A is hydrogen or a cation, with the proviso that in each group CHR'—CHR" one of R' and R" is hydrogen and the other one is $(-S)_m (-R^1)_n-R^2$.

Another aspect of the present invention is a composition that comprises a liquid diluent and at least one above-mentioned esterified cellulose ether.

Yet another aspect of the present invention is a solid dispersion that comprises at least one active ingredient dispersed in at least one above-mentioned esterified cellulose ether.

Yet another aspect of the present invention is a dosage form that is coated with at least one above-mentioned esterified cellulose ether.

Yet another aspect of the present invention is a capsule shell that comprises at least one above-mentioned esterified cellulose ether.

Yet another aspect of the present invention is a process for producing an above-mentioned esterified cellulose ether, wherein a cellulose ether is esterified with a substituted succinic anhydride of formula I

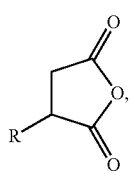

wherein R is $(-S)_m(-R^1)_n-R^2$, wherein $R^1$ is a hydrocarbon group having 1 to 4 carbon atoms, $R^2$ is an optionally substituted 5- or 6-membered cyclic group, and m and n each independently are 0 or 1.

Detailed Description

The esterified cellulose ether has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylating agent, e.g. a methylating agent, and/or a hydroxyalkylating agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further alkylated or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.90, more preferably 0.12 to 0.70, most preferably 0.15 to 0.60, and particularly 0.21 to 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention preferably have a DS(alkoxyl) in the range of 1.0 to 2.5, more preferably from 1.1 to 2.4, even more preferably from 1.2 to 2.2, most preferably from 1.6 to 2.05, and particularly from 1.7 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention has groups of formula $-C(O)-CHR'-CHR''-COOA$, wherein R' and R'' are hydrogen or $(-S)_m(-R^1)_n-R^2$, wherein $R^1$ is a hydrocarbon group having 1 to 4 carbon atoms, $R^2$ is an optionally substituted 5- or 6-membered cyclic group, m and n each independently are 0 or 1, and A is hydrogen or a cation, with the proviso that in each group CHR'—CHR'' one of R' and R'' is hydrogen and the other one is $(-S)_m(-R^1)_n-R^2$.

$R^1$ is preferably $CH_2$, $CH_2-CH_2$, $CH_2-CH_2-CH_2$ or $CH_2-CH_2-CH_2-CH_2$, more preferably $CH_2$ or $CH_2-CH_2$, and most preferably $CH_2$. In one aspect of the invention m is 1; in another aspect m is 0. The integer n is 0 or 1, more preferably n is 1. The most preferred meaning for A is hydrogen. If A is a cation, it is preferably an ammonium cation, such as $NH_4^+$ or an alkali metal ion, such as the sodium or potassium ion, more preferably the sodium ion.

$R^2$ is an optionally substituted 5- or 6-membered cyclic group, preferably an optionally substituted 6-membered cyclic group. The 5- or 6-membered cyclic group may be substituted, e.g., with a $C_{1-4}$-alkyl group, such as methyl, ethyl, n-propyl, isopropyl, n-butyl, iso-butyl or tert-butyl. A preferred example of a substituted 6-membered cyclic group is tert-butylphenyl. Non-substituted 5- or 6-membered groups are preferred. Accordingly, examples of non-substituted 5- or 6-membered cyclic groups are listed below, however the present invention is not limited to them.

$R^2$ may be an alicyclic, aromatic, or heterocyclic optionally substituted 5- or 6-membered group. The terms "alicyclic group" and "aromatic group" as used herein designate homocyclic groups. Alicyclic or aromatic optionally substituted 5- or 6-membered groups are preferred, more preferred are alicyclic or aromatic optionally substituted 6-membered groups.

Exemplary of alicyclic groups are cyclopentyl, cyclopentenyl, cyclopentadienyl, cyclohexyl, cyclohexenyl, 1,3-cyclohexadienyl or 1,4-cyclohexadienyl. The preferred alicyclic group is cyclohexyl. Phenyl is the preferred aromatic group. Heterocyclic optionally substituted 5- or 6-membered groups may be saturated or unsaturated. Exemplary of unsaturated 5-membered heterocyclic groups are pyrrolyl, furanyl and thiofuranyl. Exemplary of unsaturated 6-membered heterocyclic groups are imidazolyl, pyrazolyl, oxazolyl, isoxazolyl, thiazolyl, isothiazolyl, pyridinyl, pyranyl, thiopyranyl, a diazinyl group, such as pyrazinyl, pyrimidinyl or pyridazinyl, an oxyzinyl group, a thiazinyl group, or a dioxinyl group. Exemplary of saturated 5-membered heterocyclic groups are pyrrolidinyl, tetrahydrofuranyl and thiolanyl (tetrahydrothiophenyl). Exemplary of saturated 5-membered heterocyclic groups are imidazolidinyl, pyrazolidinyl, oxazolinidyl, isooxazolinidyl, thiazolininyl, isothiazolininyl, dioxolanyl, dithiolanyl, piperidinyl, oxanyl, or thianyl, piperazinyl, morpholinyl, thiomorpholinyl, dioxanyl, dithianyl, trioxanyl.

The esterified cellulose ethers generally have a degree of substitution of groups of formula —C(O)—CHR'—CHR"—COOA of 0.05 to 1.6, preferably of 0.1 to 1.3, more preferably of 0.2 to 1.2, and most preferably of 0.3 to 1.1.

The content of the ether and ester groups in the esterified cellulose ethers of the present invention are determined as described in the Examples section. By convention, the weight percent of a substituent is an average weight percentage based on the total weight of the cellulose repeat unit, including all substituents. The content of the methoxyl group is determined based on the mass of the methoxyl group (i.e., —OCH$_3$). The content of the hydroxyalkoxyl group is determined based on the mass of the hydroxyalkoxyl group (i.e., —O-alkylene-OH); such as hydroxypropoxyl (i.e., —O—CH$_2$CH(CH$_3$)—OH). The content of the group of formula —C(O)—CHR'—CHR"—COOA is calculated based on the mass of this group.

The esterified cellulose ethers of the present invention generally have a weight average molecular weight M$_w$ of from 10,000 to 400,000 Dalton, or from 10,000 to 250,000 Dalton, or from 12,000 to 90,000 Dalton, or from 12,000 to 70,000 Dalton, or from 15,000 to 50,000 Dalton. The esterified cellulose ethers of the present invention generally have a number average molecular weight M$_n$ of from 8000 to 150,000 Dalton, or from 9000 to 50,000 Dalton, or from 10,000 to 30,000 Dalton.

According to the process of the present invention a cellulose ether is esterified with a substituted succinic anhydride of formula I

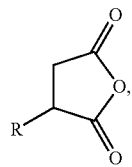

wherein R is (—S)$_m$(—R$^1$)$_n$—R$^2$, wherein R$^1$, R$^2$, m and n have the meanings described further above.

Preferably a cellulose ether is used as a starting material which has the type of ether groups and the degree(s) of substitution of ether groups as described further above. The cellulose ether generally has a viscosity of from 1.2 to 200 mPa·s, preferably from 2.4 to 100 mPa·s, more preferably from 2.5 to 50 mPa·s, and in particular from 3 to 30 mPa·s, measured as a 2 weight-% aqueous solution at 20° C. The 2.0% by weight solution of a cellulose ether in water is prepared according to United States Pharmacopeia (USP 35, "Hypromellose", pages 3467-3469), followed by an Ubbelohde viscosity measurement according to DIN 51562-1: 1999-01 (January 1999). Cellulose ethers of such viscosity can be obtained by subjecting a cellulose ether of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent. Cellulose ethers having a viscosity of less than 2.4 mPa·s, measured as a 2 weight-% aqueous solution at 20° C., and their production are described in the international patent applications WO2009061821 and WO2009/061815.

The utilized amount of the substituted succinic anhydride of formula I depends on the desired degree of esterification to be obtained in the final product, usually it is 1 to 10 times the stoichiometric amounts of the desired molar degree of substitution of the anhydroglucose units by esterification.

The esterification of the cellulose ether is typically conducted in an aliphatic carboxylic acid as a reaction medium, such as acetic acid, propionic acid, or butyric acid. The reaction medium can comprise minor amounts of other solvents or diluents which are liquid at room temperature and do not react with the cellulose ether, such as halogenated C$_1$-C$_3$ derivatives, such as dichloro methane, or dichloro methyl ether, but the amount of the aliphatic carboxylic acid is preferably more than 50 percent, more preferably at least 75 percent, and even more preferably at least 90 percent, based on the total weight of the reaction medium. Most preferably the reaction medium consists of an aliphatic carboxylic acid. The esterification reaction is generally conducted in the presence of 100 to 2,000 parts by weight of an aliphatic carboxylic acid as the reaction medium per 100 parts by weight of the cellulose ether.

The esterification reaction is generally conducted in the presence of an esterification catalyst, preferably in the presence of an alkali metal carboxylate, such as sodium acetate or potassium acetate. The amount of the alkali metal carboxylate is preferably 20 to 200 parts by weight of the alkali metal carboxylate per 100 parts by weight of the cellulose ether.

The mixture is generally heated at 60° C. to 110° C., preferably at 70 to 100° C., for a period of time sufficient to complete the reaction, that is, typically from 2 to 25 hours, more typically from 2 to 8 hours. The cellulose ether as the starting material is not always soluble in the aliphatic carboxylic acid, but can only be dispersed in or swollen by the aliphatic carboxylic acid, especially when the degree of substitution in the cellulose ether is relatively small. The esterification reaction can take place even with such a dispersed or swollen cellulose ether and, as the esterification reaction proceeds, the cellulose ether under reaction generally dissolves in the reaction medium, to finally give a homogeneous solution. After completion of the esterification reaction, the reaction product can be precipitated from the reaction mixture in a known manner, for example by contacting it with a large volume of water, such as described in U.S. Pat. No. 4,226,981, International Patent Application WO 2005/115330 or European Patent Application EP 0 219 426.

Another aspect of the present invention is a composition comprising a liquid diluent and one or more of the above described esterified cellulose ethers. The term "liquid diluent" as used herein means a diluent that is liquid at 25°

C. and atmospheric pressure. The diluent can be water or an organic liquid diluent or a mixture of water and an organic liquid diluent. Preferably the amount of the liquid diluent is sufficient to provide sufficient fluidity and process ability to the composition for the desired usage, such as spray-drying or for coating purposes.

The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. The esterified cellulose ethers of the present invention exhibit a reasonably good solubility in such organic diluents.

In one embodiment the composition of the present invention comprises as liquid diluent an organic diluent alone or mixed with a minor amount of water. In this embodiment the composition of the present invention preferably comprises more than 50, more preferably at least 65, and most preferably at least 75 weight percent of an organic liquid diluent and preferably less than 50, more preferably up to 35, and most preferably up to 25 weight percent of water, based on the total weight of the organic liquid diluent and water. This embodiment of the invention is of particularly useful if the present invention comprises an active ingredient of poor water solubility.

In another embodiment the composition of the present invention comprises as liquid diluent water alone or mixed with a minor amount of an organic liquid diluent as described above. In this embodiment the composition of the present invention preferably comprises at least 50, more preferably at least 65, and most preferably at least 75 weight percent of water and preferably up to 50, more preferably up to 35, and most preferably up to 25 weight percent of an organic liquid diluent, based on the total weight of the organic liquid diluent and water. This embodiment of the invention is particularly useful for providing coatings or capsules from aqueous compositions comprising the esterified cellulose ether of the present invention. When preparing an aqueous solution, it is preferred that at least a portion of the groups of formula —C(O)—R—COOA are in their salt form.

The composition of the present invention comprising a liquid diluent and one or more of the above described esterified cellulose ethers is useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has an aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers. The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The liquid composition of the present invention preferably comprises from 1 to 40 percent, more preferably from 5 to 35 percent, even more preferably from 7 to 30 percent, and most preferably from 10 to 25 percent of at least one esterified cellulose ether as described above, from 40 to 99 percent, more preferably from 50 to 94.9 percent, even more preferably from 65 to 92.5 percent and most preferably from 70 to 89 percent of a liquid diluent described further above, and from 0 to 40 percent, more preferably from 0.1 to 40 percent, even more preferably from 0.5 to 25 percent, and most preferably from 1 to 15 percent of an active ingredient, based on the total weight of the composition.

In one aspect of the invention the composition comprising at least one esterified cellulose ether as described above, one or more active ingredients and optionally one or more adjuvants can be used in liquid form, for example in the form of a suspension, a slurry, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with water as described above.

In another aspect of the invention the liquid composition of the present invention is used for producing a solid dispersion comprising at least one active ingredient, such as a drug described further above, at least one esterified cellulose ether as described above and optionally one or more adjuvants. The solid dispersion is produced by removing the liquid diluent from the composition.

One method of removing the liquid diluent from the liquid composition is by casting the liquid composition into a film or a capsule or by applying the liquid composition onto a solid carrier that in turn may comprise an active ingredient. The use of the liquid composition of the present invention for coating purposes is a preferred aspect of the present invention.

A preferred method of producing a solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7-page 35, line 25. Alternatively, the solid dispersion of the present invention may be prepared by i) blending a) at least one esterified cellulose ether defined above, b) one or more active ingredients and c) one or more optional additives, and ii) subjecting the blend to extrusion. The term "extrusion" as used herein includes processes known as injection molding, melt casting and compression molding. Techniques for extruding, preferably melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The solid dispersion of the present invention preferably comprises from 20 to 99.9 percent, more preferably from 30 to 98 percent, and most preferably from 60 to 95 percent of an esterified cellulose ether a) as described above, and preferably from 0.1 to 80 percent, more preferably from 2 to 70 percent, and most preferably from 5 to 40 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, consists of one or more of the adjuvants c) as described below. The solid dispersion can comprise one or more of the esterified cellulose ethers a), one or more of the active ingredients b), and optionally one or more of the adjuvants c), however their total amount is generally within the above-mentioned ranges.

Once the solid dispersion comprising at least one active ingredient in at least one esterified cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms. The solid dispersion of the present invention may be in various forms, such as in the form of strands, pellets, granules, pills, tablets, caplets, microparticles, fillings of capsules or injection molded capsules or in the form of a powder, film, paste, cream, suspension or slurry.

The amount of the active ingredient in the dosage form is generally is at least 0.1 percent, preferably at least 1 percent, more preferably at least 3 percent, most preferably at least 5 percent and generally up to 70 percent, preferably up to 50 percent, more preferably up to 30 percent, most preferably up to 25 percent, based on the total weight of the dosage form.

In another aspect of the invention the composition of the present invention comprising a liquid diluent and one or more of the above described esterified cellulose ethers may be used for coating dosage forms, such as tablets, granules, pellets, caplets, lozenges, suppositories, pessaries or implantable dosage forms, to form a coated composition. If the composition of the present invention comprises an active ingredient, such as a drug, drug layering can be achieved, i.e., the dosage form and the coating may comprise different active ingredients for different end-uses and/or having different release kinetics.

In yet another aspect of the invention the composition of the present invention comprising a liquid diluent and one or more of the above described esterified cellulose ethers may be used for the manufacture of capsules in a process which comprises the step of contacting the liquid composition with dipping pins.

The liquid composition and the solid dispersion of the present invention may further comprise optional additives, such as coloring agents, pigments, opacifiers, flavor and taste improvers, antioxidants, and any combination thereof. Optional additives are preferably pharmaceutically acceptable. Useful amounts and types of one or more optional adjuvants are generally known in the art and depend on the intended end-use of the liquid composition or the solid dispersion of the present invention.

Some embodiments of the invention will now be described in detail in the following Examples.

EXAMPLES

Unless otherwise mentioned, all parts and percentages are by weight. In the Examples the following test procedures are used.

Abbreviations:
Cy-SA: cyclohexyl succinic anhydride
Cy-S-SA: (cyclohexylthio) succinic anhydride
Ph-S-SA: (phenylthio) succinic anhydride
Bn-S-SA: (benzylthio) succinic anhydride
nBu-SA: n-butylsuccinic anhydride
HPMC: hydroxypropyl methyl cellulose
HPMCAS: hydroxypropyl methyl cellulose acetate succinate
HPMC-nBu: hydroxypropyl methylcellulose n-butylsuccinate Content of Ether and Ester Groups The content of the methoxy and hydroxypropoxy groups in HPMCAS and in HPMC-C(O)—CHR'—CHR"—COOH were determined as described for "Hypromellose", in United States Pharmacopeia and National Formulary, USP 35, pp 3467-3469.

The ester substitution with acetyl groups (—CO—CH$_3$) and with succinoyl groups (—CO—CH$_2$—CH$_2$—COOH) in HPMCAS were determined following the monograph by United States Pharmacopia and National Formulary, NF 29, pp. 1548-1550 for Hypromellose Acetate Succinate.

The ester substitution with C(O)—CHR'—CHR"—COOH groups in HPMC-C(O)—CHR'—CHR"—COOH were determined by $^1$H NMR spectroscopy. The number-average molar mass of cellulose ether (e.g., HPMC) was determined by size exclusion chromatography that was equipped with a light scattering and a refractive index detector (see below), from which the number of protons in one cellulose ether chain was determined. Then from the $^1$H NMR sprectra of HPMC-C(O)—CHR'—CHR"—COOH, the degree of substitution of the introduced esters was determined by comparing the integration of protons from the R' and R" to that of the cellulose ether precursor.

In line with the procedure described in the above-mentioned United States Pharmacopia and National Formulary, HPMC or HPMCAS was hydrolyzed using hydroiodic acid and the content of methyl iodide and isopropyl iodide were quantified by HPLC. $^1$H and $^{13}$C NMR spectra were recorded on a Bruker AV-500, Varian Inova 500, or a Varian Inova 300 spectrometer at 23° C. with DMSO-d$_6$ or CDCl$_3$ as the solvent unless otherwise specified.

Number-Average Molar Mass M$_n$ and Weight-average molar mass M$_w$

Number-average molar mass M$_n$ and weight-average molar mass M$_w$ were determined by size-exclusion chromatography (SEC).

The SEC measurement of HPMC was carried out on an Agilent 1260 liquid chromatograph with 0.1 M Na$_2$SO$_4$ aqueous solution (supplemented with 1% acetic acid) as the mobile phase. The SEC housed a Eprogen (Downers Grove, Ill.) CATSEC guard column and three separating columns with pore sizes of 1000, 300, and 100 Å, respectively. The detectors were an Agilent 1260 MWD UV-vis detector, a Wyatt Dawn Heleos II light-scattering detector, and a Wyatt Optilab T-rEX refractive-index detector.

The SEC measurement of HPMC esters of substituted succinates was carried out on an Agilent 1260 liquid chromatograph with tetrahydrofuran (THF) as the mobile phase. The SEC housed a Waters Styragel guard column and three separating columns that cover an effective molecular weight range of 100-10,000,000 g mol$^{-1}$. The detectors were an Agilent 1260 VWD UV-vis detector, a Wyatt Dawn Heleos II light-scattering detector, and a Wyatt Optilab T-rEX refractive-index detector.

Synthesis of Substituted Succinic Anhydrides

The synthesis of cyclohexylsuccinic anhydride, Cy-SA, was carried out following the published procedure toward cyclopentylsuccinic anhydride (Bergmeier, S. C.; Ismail, K. A. *Synthesis-Stuttgart* 2000, (10), 1369-1371) and the product was purified via vacuum distillation. (Rowley, J. M.; Lobkovsky, E. B.; Coates, G. W. *Journal of the American Chemical Society* 2007, 129, (16), 4948-4960.)

The synthesis of (phenylthio) succinic anhydride, Ph-S-SA (Rowley, J. M.; Lobkovsky, E. B.; Coates, G. W. *Journal of the American Chemical Society* 2007, 129, (16), 4948-4960) and (benzylthio) succinic anhydride, Bn-S-SA, (Kaydos, J. A.; Smith, D. L. *Journal of Organic Chemistry* 1983, 48, (7), 1096-1099) was carried out following published procedures, except that the product was purified via column chromatography followed by vacuum distillation. Ph-S-SA: $R_f$ (retention factor)=0.54 in hexane/ethyl acetate=8:2 (v/v), bp=120° C. at 65 mTorr. Bn-S-SA: $R_f$=0.75 in hexane/ethyl acetate=8:2 (v/v), bp=140° C. at 55 mTorr.

The detailed synthetic procedure of (cyclohexylthio) succinic anhydride, Cy-S-SA, is described as below. 11.3 mL of cyclohexanethiol (9.2×10$^{-2}$ mol), 9.0 g of maleic anhydride (9.2×10$^{-2}$ mol), and 256 µL of triethylamine (9.2×10$^{-4}$ mol) were dissolved in 75 mL of benzene, and the reaction was allowed to proceed for 3.0 h at 70° C. Then 200 µL of concentrated sulfuric acid was added into the mixture to quench the reaction. The mixture was filtered and concentrated to afford dark red crude product. Further purifications with flash chromatography ($R_f$=0.49 in hexane/ethyl acetate=8:2, v/v) followed by fractional distillation (bp=110° C. at 55 mTorr) gave nearly colorless, slightly yellow oil.

Examples 1-10 and Comparative Example A

Synthesis of HPMC Esters of Substituted Succinates

The synthesis of the HPMC esters of substituted succinates is illustrated below. HPMC and the HPMC esters are illustrated by the formulas below. It should be noted that the structures of HPMC and HPMC-(R-SA) given below are only for illustrative purposes. They neither reflect the actual regiochemistry and nor the actual MS(hydroxypropoxyl), DS(methoxyl) or DS(C(O)—CHR'—CHR"—COOA), abbreviated as DS(succinate).

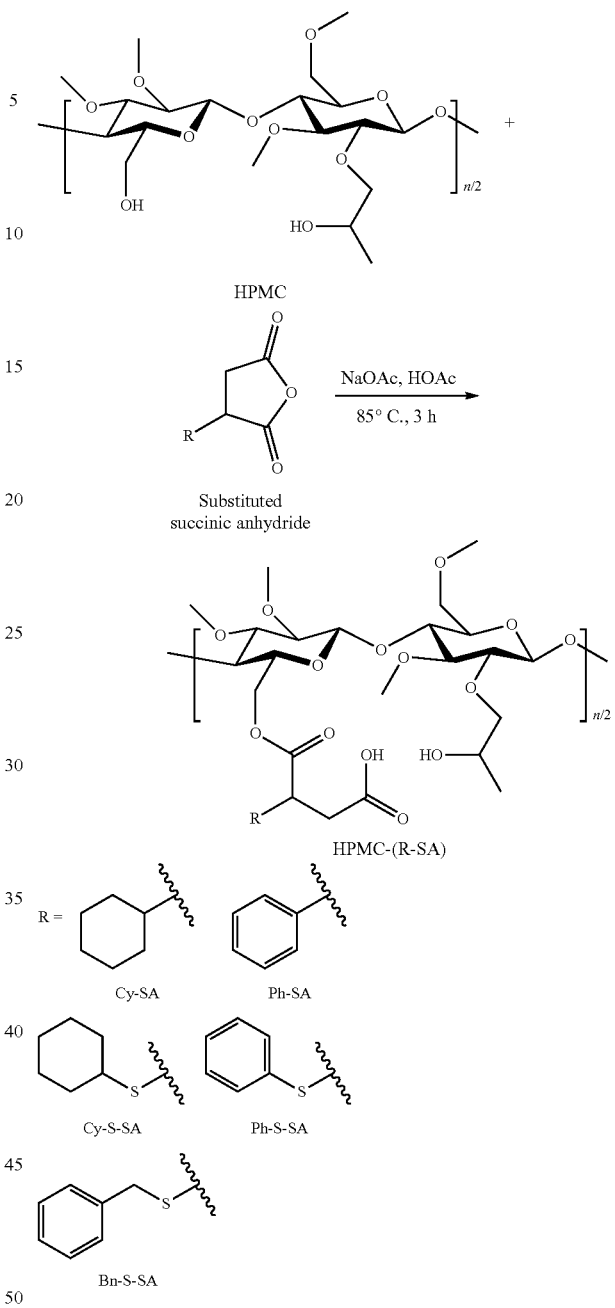

The composition of HPMC, sodium acetate, and acetic acid in the feed was kept the same and a homogeneous mixture was first allowed to form at 85° C. ([—OH]$_0$:[NaOAc]$_0$=1:2, and [—OH]$_0$≈0.4 M, wherein [—OH]$_0$:[NaOAc]$_0$ is the ratio of the initial concentration of hydroxyls in HPMC to that of the initial concentration of sodium acetate in the feed and [—OH]$_0$≈0.4 M means that the initial concentration of hydroxyls on HPMC in acetic acid is about 0.4 molar. The HPMC had a DS(methoxyl) of 1.91, an MS(hydroxypropoxyl) of 0.25, a viscosity of about 3 mPa·s, measured as a 2 weight-% aqueous solution at 20° C., an $M_n$ of 11.8 kg/mol and an $M_w$ of 15.7 kg/mol, determined by SEC. The 2.0% by weight solution of a cellulose ether in water is prepared according to United States Pharmacopeia (USP 35, "Hypromellose", pages 3467-3469), followed by an Ubbelohde viscosity measurement according to DIN 51562-1:1999-01 (January 1999).

Next, the specific amount of an anhydride was added to target the specific substituent and degree of substitution, as listed in Table 1 below. The reaction was allowed to proceed at 85° C. for 3.0 h before it was quenched by adding DI (deionized) water into the mixture. The mixture was then precipitated into water. The detailed procedures for synthesizing HPMC-Ph-0.63 of Example 4, HPMC-CyS-0.72 of Example 7 and HPMC-nBu-0.51 of Comparative Example A are listed below as representative procedures.

Example 4

Synthesis of HPMC-Ph-0.63

3.40 g of HPMC (pendent hydroxyl: $1.8 \times 10^{-2}$ mol), 3.01 g of sodium acetate ($3.7 \times 10^{-2}$ mol), and 35 mL of glacial acetic acid were charged into a 100-mL round bottom flask, and were allowed to form a homogeneous mixture at 85° C. with magnetic stirring. After that, 6.5 g of phenylsuccinic anhydride ($3.7 \times 10^{-2}$ mol) was added into the flask. The reaction was allowed to proceed at 85° C. for 3.0 h, before it was quenched by adding 10 mL of DI (deionized) water into the mixture. The product was isolated by precipitation into 1.0 L of water three times, and further dried under vacuum at 22° C. until constant weight was achieved.

acetic acid were charged into a 50-mL round bottom flask, and allowed to form a homogeneous mixture at 85° C. with magnetic stirring. After that, 1.44 g of nBu-SA ($9.2 \times 10^{-3}$ mol) was added into the flask. The reaction was allowed to proceed at 85° C. for 3.0 h before it was quenched by adding 3 mL of DI water into the mixture. The mixture was first precipitated into 500 mL of water, redissolved in 20 mL of THF and precipitated into 500 mL of water for three more times, and further dried under vacuum at 22° C. until constant mass was achieved. The product was white, slightly yellow powder.

Comparative Example B

Comparative Example B was hydroxypropyl methyl cellulose acetate succinate (HPMCAS) derived from the same HPMC as used for preparing Examples 1-10 and Comparative Example A. The HPMCAS had a $DS_{acetyl}$ of 0.57 and a $DS_{succinoyl}$ of 0.28 and was commercially available from The Dow Chemical Company as AFFINISOL™ HPMCAS 912 G.

TABLE 1

| (Comp.) Example | Sample | Anhydride[a] | [—OH]$_0$:[Anhydride]$_0$[b] | DS[c] | $M_n$ SEC (kg/mol) | $M_w$ SEC (kg/mol) |
|---|---|---|---|---|---|---|
| 1 | HPMC-Cy-0.57 | CySA | 1:3 | 0.57 | 16.9 | 26.2 |
| 2 | HPMC-Ph-0.24 | PhSA | 1:0.5 | 0.24 | 24.6 | 83.3 |
| 3 | HPMC-Ph-0.44 | PhSA | 1:1 | 0.44 | 15.6 | 23.1 |
| 4 | HPMC-Ph-0.63 | PhSA | 1:2 | 0.63 | 17.2 | 26.2 |
| 5 | HPMC-CyS-0.42 | Cy-S-SA | 1:0.7 | 0.42 | 17.9 | 26.0 |
| 6 | HPMC-CyS-0.57 | Cy-S-SA | 1:1 | 0.57 | 19.8 | 28.3 |
| 7 | HPMC-CyS-0.72 | Cy-S-SA | 1:2 | 0.72 | 21.3 | 30.8 |
| 8 | HPMC-CyS-0.99 | Cy-S-SA | 1:5 | 0.99 | 23.5 | 33.3 |
| 9 | HPMC-PhS-0.62 | Ph-S-SA | 1:1 | 0.62 | 17.9 | 25.3 |
| 10 | HPMC-BnS-0.57 | Bn-S-SA | 1:1 | 0.57 | 19.5 | 28.5 |
| A | HPMC-nBu-0.51 | nBu-SA | 1:2 | 0.51 | n.a | n.a. |

[a]The kind of anhydride used in the synthesis of the specific sample.
[b]The ratio of the initial concentration of hydroxyls on HPMC to that of anhydride in the feed.
[c]Degree of substitution of the succiniate in the isolated HPMC-(R-SA) as determined by $^1$H NMR spectroscopy.
n.a.: not assessed Example 7

Synthesis of HPMC-CyS-0.72

0.87 g of HPMC (pendent hydroxyl: $4.7 \times 10^{-3}$ mol), 0.77 g of sodium acetate ($9.4 \times 10^{-3}$ mol), and 11.0 mL of glacial acetic acid were charged into a 50-mL round bottom flask, and were allowed to form a homogeneous mixture at 85° C. with magnetic stirring. After that, 2.0 g of cylcohexylthiosuccinic anhydride, Cy-S-SA, ($9.4 \times 10^{-3}$ mol) was added into the flask. The reaction was allowed to proceed at 85° C. for 3.0 hr before it was quenched by adding 5 mL of DI water into the mixture. The mixture was first precipitated into 1.0 L of water, redissolved in 20 mL of THF, precipitated into 1.0 L of water once more, and further dried under vacuum at 22° C. until constant weight was achieved. The product was white, slightly yellow powder.

Comparative Example A

HPMC n-Butylsuccinate (comparative, but not prior art)

0.85 g of HPMC (pendent hydroxyl: $4.6 \times 10^{-3}$ mol), 0.75 g of sodium acetate ($9.4 \times 10^{-3}$ mol), and 10.0 mL of glacial Preparation of Spray-dried dispersions (SDDs)

SDDs were made at lab scale, and the following procedure for HPMC-CyS-0.72 (Example 7) at 10 wt % phenytoin loading serves as an example. 225 mg of HPMC-CyS-0.72 and 25.0 mg of phenytoin were first mixed in 12.25 g of acetone (corresponding to the concentration of total solids as 2.0 wt %) to form a homogeneous solution with magnetic stirring. The solution was loaded in a 20-mL syringe on a syringe pump and SDDs were prepared with a Mini-sprayer (Bend Research, Bend, Oreg.) at the following conditions: inlet temperature, 68° C.; $N_2$ flow rate, 12.8 L min$^{-1}$; solution flow rate, 0.65 mL min$^{-1}$. The outlet temperature was between 22 and 28° C. The spray-dried powders were collected with the aid of an anti-static bar and further dried under vacuum (10 mTorr) for at least 12 h.

All samples were spray-dried from acetone solutions, except those with HPMC-Ph-0.24, which were dried from THF solutions. (At 22° C., HPMC-Ph-0.24 was fully soluble in THF at 2.0 wt %, but not in acetone). SDDs with phenytoin were stored in a vacuum desiccator at 22° C.

The same procedure was used to produce SDDs of 25 wt % of the drug phenytoin in HPMC esters of substituted succinates and to produce SDDs of 10 wt % or 25 wt % of the drug probucol in HPMC esters of substituted succinates.

Scanning Electron Microscopy (SEM)

Samples to be analyzed were spread with a spatula onto a carbon conductive tape (Ted Pella Inc), and then coated with 10 nm Au/Pd (60/40 by weight) in a 15 mTorr Argon atmosphere using a Denton DV-502A high vacuum deposition system. Samples were imaged using a secondary electron detector on a Hitachi S-900 field emission gun SEM. The accelerating voltage was 1.2 or 3.0 kV. The magnification was between 3,000 and 30,000.

FIG. 1 represents SEM pictures of crystalline phenytoin (as received). The crystals look as columnar particles with fine layered structures. The particles are mostly 1-50 μm in the largest dimension. Scale bars: (a) 5.0 μm and (b) 1.0 μm.

Figure 2:
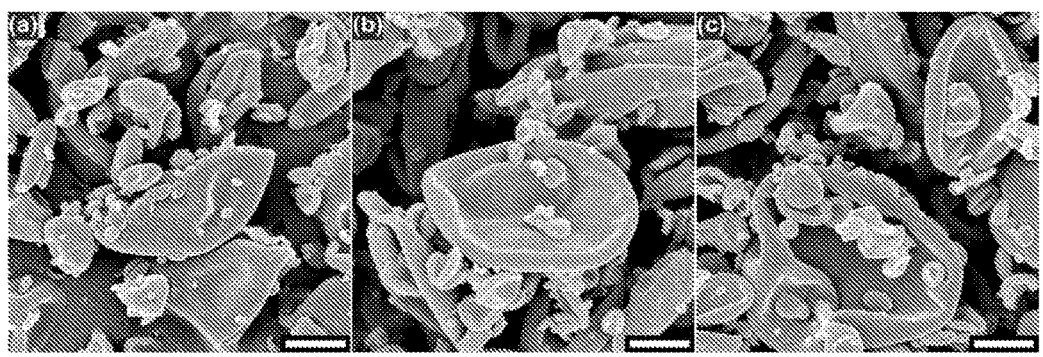
FIG. 2-5 represent SEM pictures of solid dispersions of phenytoin in esterified cellulose ethers.

FIG. 2 represents SEM pictures of SDDs of phenytoin with (a) HPMC-Cy-0.57 (b) HPMC-PhS-0.62, and (c) HPMC-BnS-0.57 as the matrix materials at 10 wt % phenytoin loading. The scale bars are 800 nm.

Figure 3:
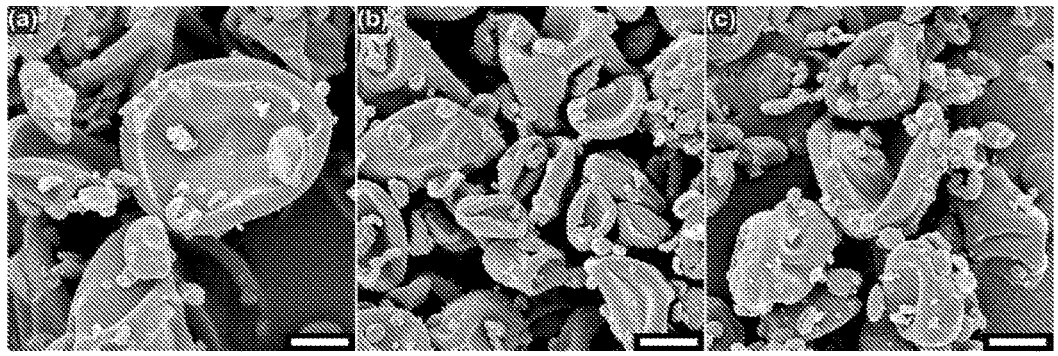

FIG. 3 represents SEM pictures of SDDs of phenytoin with three HPMC-CyS as the matrices at 10 wt % phenytoin loading: (a) HPMC-CyS-0.42, (b) HPMC-CyS-0.72, and (c) HPMC-CyS-0.99. The scale bars are 1.0 μm.

Figure 4:
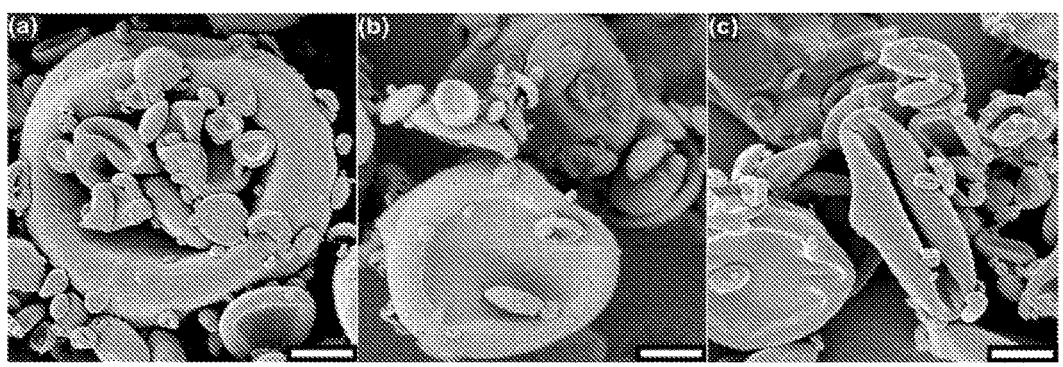

FIG. 4 represents SEM pictures of SDDs of phenytoin with (a) HPMCAS of Comparative Example B, (b) HPMC-Ph-0.63, and (c) HPMC-CyS-0.57 as the matrix materials at 10 wt % phenytoin loading. The scale bars are 800 nm.

Figure 5:
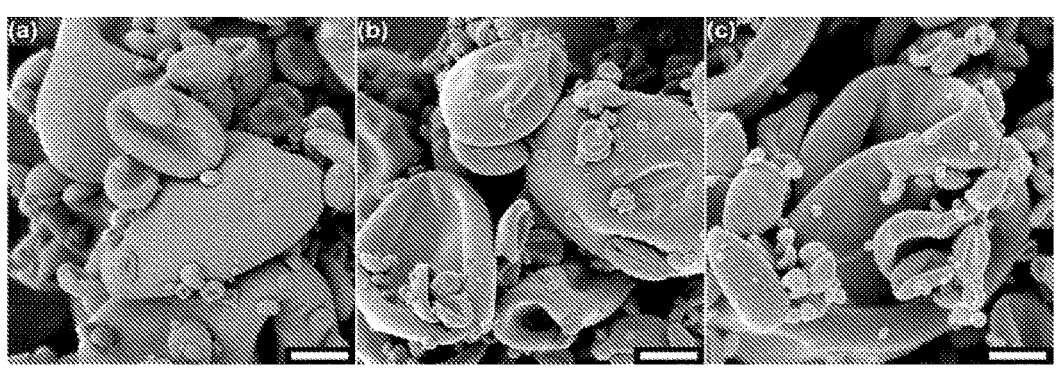

FIG. 5 represents SEM pictures of SDDs of phenytoin with (a) HPMCAS of Comparative Example B, (b) HPMC-Ph-0.63, and (c) HPMC-CyS-0.57 as the matrix materials at 25 wt % phenytoin loading. The scale bars are 600 nm.

Figure 6:
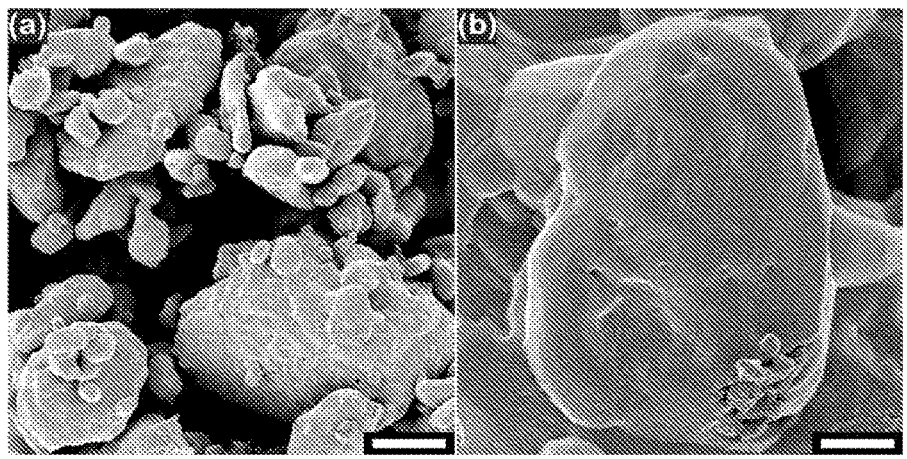
FIG. 6 represents SEM pictures of the crystalline drug probucol.

FIG. 6 represents SEM pictures of crystalline probucol (as received). The crystals are potato-like particles with irregular surfaces. The particles are mostly 1-100 μm in the largest dimension. Scale bars: (a) 10.0 μm and (b) 1.5 μm.

Figure 7:
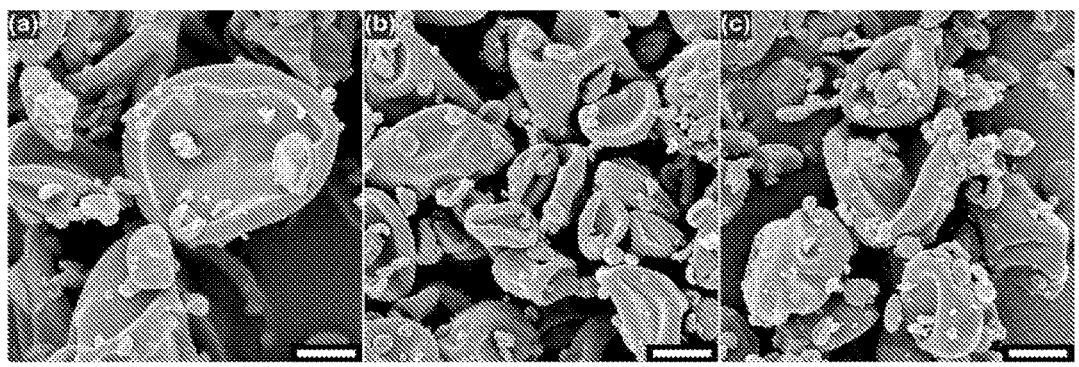
FIG. 7 represents SEM pictures of solid dispersions of probucol in esterified cellulose ethers.

FIG. 7 represents SEM pictures of SDDs at 10 wt % probucol loadings with (a) HPMCAS of Comparative Example B, (b) HPMC-Ph-0.63, and (c) HPMC-CyS-0.57 as the matrices, respectively. The scale bars indicate 1.5 μm.

Powder X-Ray diffraction (powder XRD)

Powder samples (~50 mg) were packed in a 0.5 mm deep zero-background holder and analyzed on a Bruker-AXS D5005 diffractometer at 22° C. The X-ray source (Cu, λ=1.54 Å) was operated at a voltage of 45 kV and a current of 40 mA. Data were collected from 5 to 400 (2θ) with a step size of 0.02° and a scan rate of 1 second/step. In FIG. 8-11 the unit "I (a.u.)" means "intensity (arbitrary units)".

Figure 8:
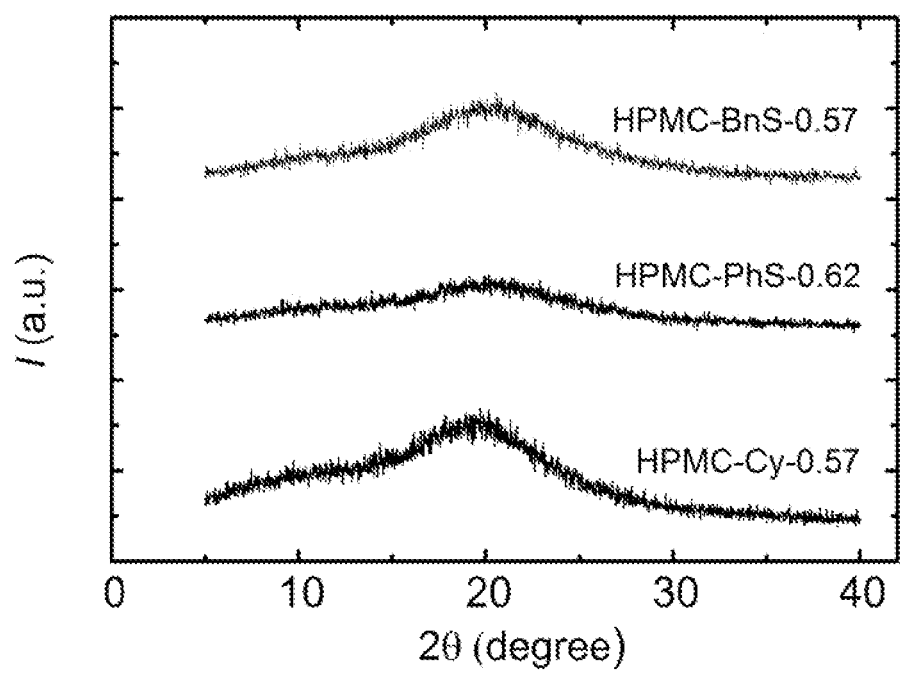
FIG. 8-11 represent powder X-Ray diffraction patterns of solid dispersions of phenytoin in esterified cellulose ethers and of crystalline phenytoin.

FIG. 8, from bottom to top, represents powder XRD patterns of SDDs with HPMC-Cy-0.57, HPMC-PhS-0.62, and HPMC-BnS-0.57 as the matrices at 10 wt % phenytoin loading.

Figure 9:
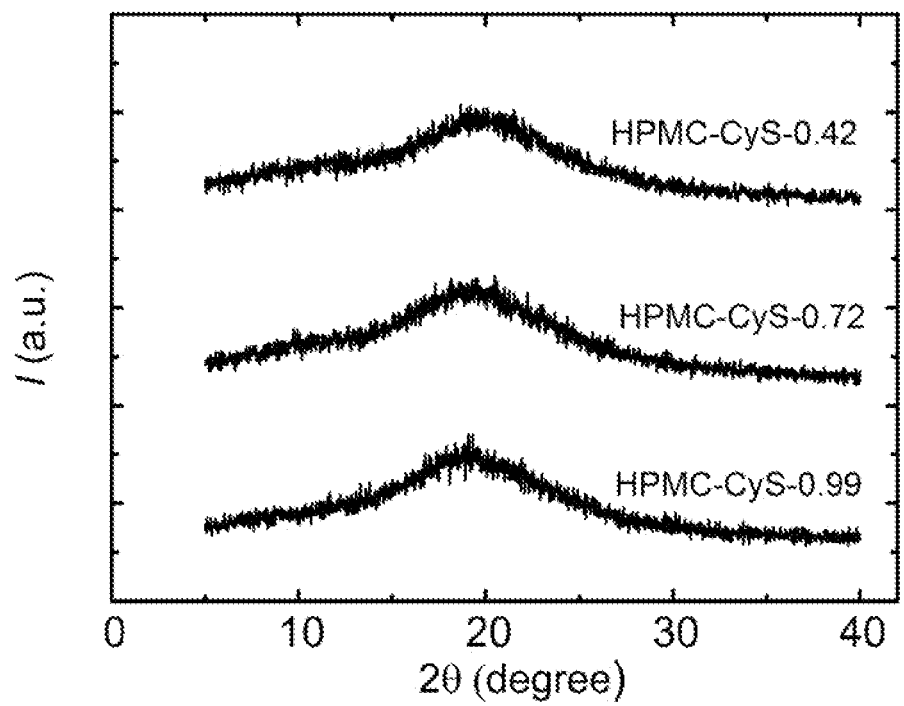

FIG. 9, from bottom to top, represents powder XRD patterns of SDDs with HPMC-CyS-0.99, HPMC-CyS-0.72, and HPMC-CyS-0.42 as the matrices at 10 wt % phenytoin loading.

Figure 10:
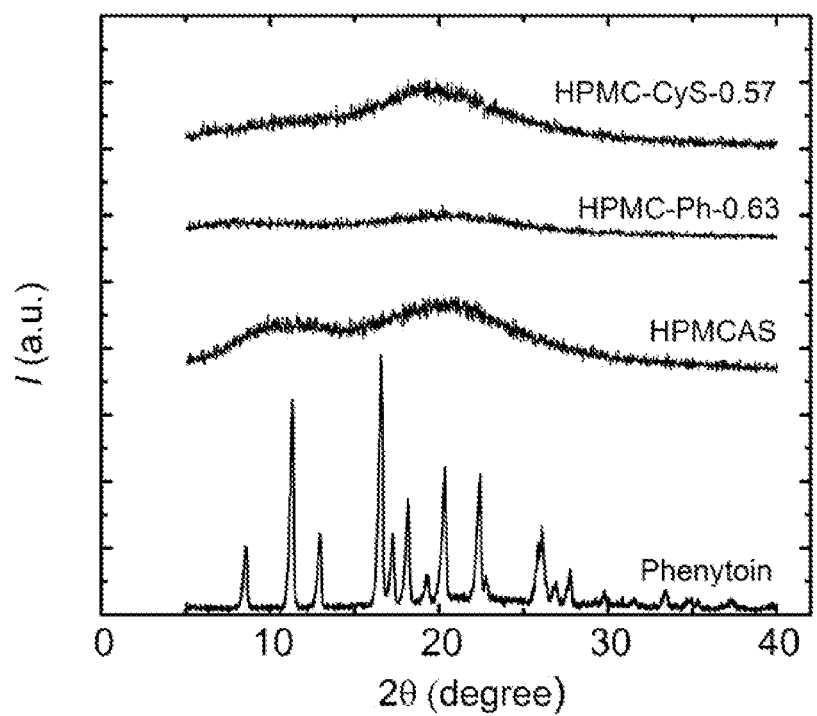

FIG. 10, from bottom to top, represents powder XRD patterns of crystalline phenytoin and SDDs with HPMCAS of Comparative Example B, HPMC-Ph-0.63, and HPMC-CyS-0.57 as the matrices at 10 wt % phenytoin loading.

Figure 11:
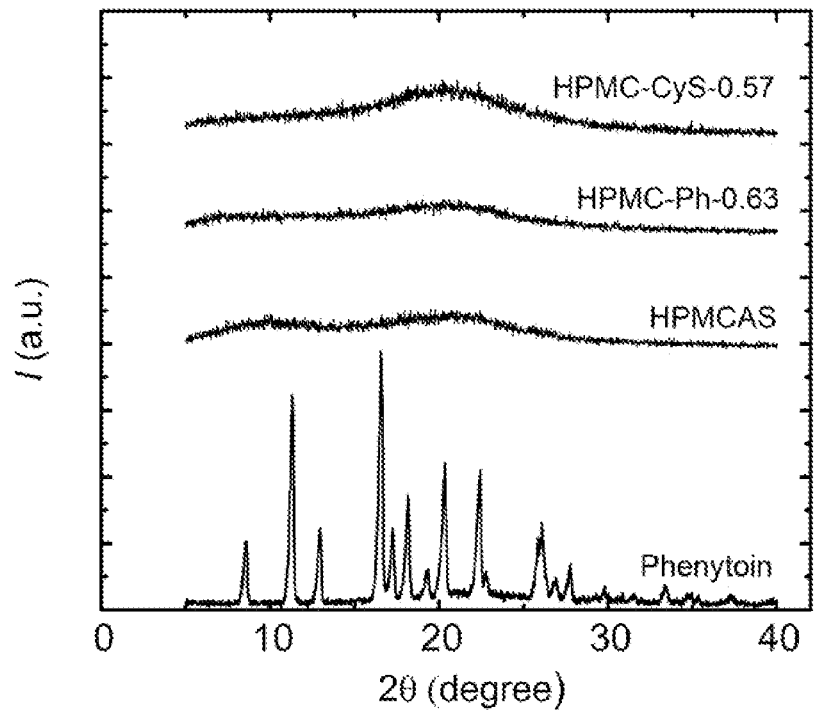

FIG. 11, from bottom to top, represents powder XRD patterns of crystalline phenytoin and SDDs with HPMCAS of Comparative Example B, HPMC-Ph-0.63, and HPMC-CyS-0.57 as the matrices at 25 wt % phenytoin loading.

All of the SDDs show broad featureless patterns, indicating minimal amount of detectable phenytoin crystals in the samples.

Dissolution Tests

Samples (either spray dried dispersions SSDs or crystalline drug) were weighed into 1.5 mL conical microcentrifuge tubes in triplicates. Phosphate buffer solution (PBS, 82 mM sodium chloride, 20 mM sodium phosphate dibasic, 47 mM potassium phosphate monobasic, 0.5 wt % simulated intestinal fluid powder, adjusted to pH 6.5 with NaOH) at 37° C. was added to in an amount that would produce a final concentration of drug of 1000 g/mL if all material was fully dissolved (e.g. 18.0 mg of spray-dried dispersion consisting of 1.8 mg of drug and 16.2 mg of polymer was diluted with 1.8 mL of buffer solution). Samples were vortexed for 1 min and set in an isothermal aluminum sample holder set at 37° C. At each time point (4, 10, 20, 40, 90, 180, and 360 min), samples were centrifuged at 13,000×g for 1 min, and a 50 μL aliquot was removed and diluted with 250 μL ethanol. The samples were again vortexed for 30 s and held at 37° C. until the next time point. Drug concentration in each aliquot was determined by reverse phase HPLC. Samples were analyzed on an Agilent 1260 liquid chromatograph system with a multi-wavelength UV-vis detector, 1260 MWD. The HPLC housed an Agilent Poroshell 120 EC-C18 column, whose size was 4.6×50 mm. The pore size was 120 Å, and the particle size was 2.7 μm. The chromatogram was monitored at 254 nm. For phenytoin, the mobile phase was 45:55 (v/v) of MeCN/Water, the elution volume of phenytoin was 1.08 mL, and a calibration was made in the range of 10-1000 μg/mL.

The results are listed in Tables 2 and 3 below for phenytoin and in Table 4 for Probucol.

TABLE 2

| (Comp.) Example | Polymer | $c_{max}$ (μg/mL)[a] | $c_{360\ min}$ (μg/mL)[b] | $AUC_{360\ min}$ (min μg/mL)[c] | EF[d] |
|---|---|---|---|---|---|
| | | 10 wt % Phenyto in in SDD | | | |
| 1 | HPMC-Cy-0.57 | 250 | 250 | $8.9 \times 10^4$ | 5.3 |
| 4 | HPMC-Ph-0.63 | 620 | 190 | $8.0 \times 10^4$ | 4.8 |
| 5 | HPMC-CyS-0.42 | 890 | 210 | $1.2 \times 10^5$ | 7.0 |
| 6 | HPMC-CyS-0.57 | 740 | 430 | $2.1 \times 10^5$ | 13 |
| 7 | HPMC-CyS-0.72 | 550 | 550 | $1.9 \times 10^5$ | 12 |
| 8 | HPMC-CyS-0.99 | 410 | 410 | $1.4 \times 10^4$ | 8.5 |
| 9 | HPMC-PhS-0.62 | 910 | 240 | $1.2 \times 10^5$ | 7.0 |
| 10 | HPMC-BnS-0.57 | 550 | 230 | $1.5 \times 10^5$ | 8.9 |
| A | HPMC-nBu-0.51 | 420 | 150 | $6.9 \times 10^4$ | 4.1 |
| B | HPMCAS | 970 | 230 | $1.1 \times 10^5$ | 6.5 |

[a]Maximum apparent concentration of phenytoin
[b]Apparent concentration of phenytoin at 360 min.
[c]Total area under the curve during the 6 h of dissolution test
[d]Enhancement factor defined as the ratio of $AUC_{360\ min}$ of a SDD to that of crystalline phenytoin. The $c_{max}$, $c_{360\ min}$ and $AUC_{360\ min}$ of crystalline phenytoin was 49 μg/mL, 48 μg/mL, and $1.7 \times 10^4$ min μg/mL, respectively.

TABLE 3

| (Comparative) Example | Polymer | $c_{max}$ (μg/mL)[a] | $c_{360\ min}$ (μg/mL)[b] | $AUC_{360\ min}$ (min μg/mL)[c] | EF[d] |
|---|---|---|---|---|---|
| | | 25 wt % Phenytoin in SSD | | | |
| 1 | HPMC-Cy-0.57 | 380 | 180 | $7.9 \times 10^4$ | 4.7 |
| 4 | HPMC-Ph-0.63 | 370 | 130 | $5.8 \times 10^4$ | 3.5 |
| 5 | HPMC-CyS-0.42 | 620 | 190 | $8.6 \times 10^4$ | 5.1 |
| 6 | HPMC-CyS-0.57 | 490 | 200 | $8.6 \times 10^4$ | 5.1 |
| 7 | HPMC-CyS-0.72 | 800 | 240 | $1.1 \times 10^5$ | 6.5 |
| 8 | HPMC-CyS-0.99 | 700 | 290 | $1.3 \times 10^5$ | 7.7 |
| 9 | HPMC-PhS-0.62 | 330 | 130 | $5.7 \times 10^4$ | 3.4 |
| 10 | HPMC-BnS-0.57 | 450 | 190 | $8.3 \times 10^4$ | 5.0 |
| A | HPMC-nBu-0.51 | 290 | 140 | $5.7 \times 10^4$ | 3.4 |
| B | HPMCAS | 460 | 190 | $7.9 \times 10^4$ | 4.7 |

[a]Maximum apparent concentration of phenytoin
[b]Apparent concentration of phenytoin at 360 min.
[c]Total area under the curve during the 6 h of dissolution test
[d]Enhancement factor defined as the ratio of $AUC_{360\ min}$ of a SDD to that of crystalline phenytoin. The $c_{max}$, $c_{360\ min}$ and $AUC_{360\ min}$ of crystalline phenytoin was 49 μg/mL, 48 μg/mL, and $1.7 \times 10^4$ min μg/mL, respectively.

TABLE 4

| (Comparative) Example | Polymer | $c_{max}$ (μg/mL)[a] | $c_{180\ min}$ (μg/mL)[b] | $AUC_{180\ min}$ (min μg/mL)[c] | $EF^d$ |
|---|---|---|---|---|---|
| | | 10 wt % Probucol in SSD | | | |
| 2 | HPMC-Ph-0.24 | 930 | 910 | $1.6 \times 10^5$ | $2.2 \times 10^4$ |
| 3 | HPMC-Ph-0.44 | 940 | 920 | $1.6 \times 10^5$ | $2.2 \times 10^4$ |
| 4 | HPMC-Ph-0.63 | 940 | 920 | $1.6 \times 10^5$ | $2.2 \times 10^4$ |
| 6 | HPMC-CyS-0.57 | 890 | 890 | $1.5 \times 10^5$ | $2.0 \times 10^4$ |
| B | HPMCAS | 980 | 980 | $1.7 \times 10^5$ | $2.3 \times 10^4$ |
| | | 25 wt % Probucol in SSD | | | |
| 2 | HPMC-Ph-0.24 | 780 | 560 | $1.2 \times 10^5$ | $1.6 \times 10^4$ |
| 3 | HPMC-Ph-0.44 | 820 | 760 | $1.4 \times 10^5$ | $1.9 \times 10^4$ |
| 4 | HPMC-Ph-0.63 | 930 | 930 | $1.6 \times 10^5$ | $2.2 \times 10^4$ |
| 6 | HPMC-CyS-0.57 | 960 | 930 | $1.6 \times 10^5$ | $2.2 \times 10^4$ |
| B | HPMCAS | 880 | 880 | $1.5 \times 10^5$ | $2.1 \times 10^4$ |

[a] Maximum apparent concentration of probucol
[b] Apparent concentration of probucol at 180 min., duration of dissolution tests
[c] Total area under the curve during the 3 h of dissolution test
[d] Enhancement factor defined as the ratio of $AUC_{180\ min}$ of a SDD to that of crystalline probucol. The solubility of crystalline probucol in water was 0.041 μg/mL (Calculated using Advanced Chemistry Development (ACD/Labs) Software V11.02 (© 1994-2013 ACD/Labs)), from which the $AUC_{180\ min}$ was calculated to be 7.3 min μg/mL.

The results in Tables 2 to 4 illustrate that that the esterified cellulose ethers of the present invention are effective at maintaining the concentration of poorly water-soluble drugs in aqueous liquids at supersaturation levels. Their effectiveness is generally comparable to and in some embodiments of the invention higher than the effectiveness of HPMCAS. Moreover, the esterified cellulose ethers of the present invention are generally more effective than HPMC alkyl succinates, such as HPMC n-butylsuccinate of Comparative Example A, particularly at a drug concentration of about 10 wt %.

The invention claimed is:

1. An esterified cellulose ether comprising groups of formula

—C(O)—CHR'—CHR"—COOA, wherein one of R' or R" is hydrogen and the other of R' of R" is $(-S)_m(-R^1)_n-R^2$, wherein $R^1$ is a hydrocarbon group having 1 to 4 carbon atoms, $R^2$ is an optionally substituted 5- or 6-membered cyclic group, m is 1, n is 0 or 1, and A is hydrogen or a cation.

2. The esterified cellulose ether of claim 1 wherein $R^1$ is $CH_2$.

3. The esterified cellulose ether of claim 1 wherein $R^2$ is non-substituted 5- or 6-membered cyclic group.

4. The esterified cellulose ether of claim 1 wherein n=0.

5. The esterified cellulose ether of claim 1 wherein $R^2$ is cyclohexyl or phenyl.

6. The esterified cellulose ether of claim 1 being an esterified hydroxyalkyl methylcellulose.

* * * * *